(12) United States Patent
Tirtowidjojo et al.

(10) Patent No.: US 8,581,011 B2
(45) Date of Patent: Nov. 12, 2013

(54) PROCESS FOR THE PRODUCTION OF CHLORINATED AND/OR FLUORINATED PROPENES

(75) Inventors: Max M. Tirtowidjojo, Lake Jackson, TX (US); Debashis Chakraborty, Lake Jackson, TX (US); Juergen Eiffler, Stade (DE); Kurt F. Hirsekorn, Midland, MI (US); William J. Kruper, Jr., Sanford, MI (US)

(73) Assignee: Dow Global Technologies, LLC, Midland, MI (US)

( * ) Notice: Subject to any disclaimer, the term of this patent is extended or adjusted under 35 U.S.C. 154(b) by 0 days.

(21) Appl. No.: 12/900,810

(22) Filed: Oct. 8, 2010

(65) Prior Publication Data

US 2011/0083955 A1    Apr. 14, 2011

Related U.S. Application Data

(60) Provisional application No. 61/250,081, filed on Oct. 9, 2009.

(51) Int. Cl.
    *C07C 21/18* (2006.01)
(52) U.S. Cl.
    USPC .......................................... 570/159; 570/160
(58) Field of Classification Search
    None
    See application file for complete search history.

(56) References Cited

U.S. PATENT DOCUMENTS

| | | | |
|---|---|---|---|
| 2,119,484 A | 5/1938 | Levine et al. | |
| 2,299,441 A | 9/1939 | Vaughan | |
| 2,179,378 A | 11/1939 | Metzger | |
| 2,302,228 A | 11/1942 | Kharasch et al. | |
| 2,370,342 A | 2/1945 | Naeher | |
| 2,435,983 A | 12/1945 | Schmerling | |
| 2,449,286 A | 9/1948 | Fairbairn | |
| 2,630,461 A | 3/1953 | Sachsse | |
| 2,688,592 A | 9/1954 | Skeeters | |
| 2,765,359 A | 10/1956 | Pichler | |
| 2,973,393 A | 2/1961 | Monroe | |
| 3,000,980 A | 9/1961 | Asadorian | |
| 3,094,567 A | 6/1963 | Eaker | |
| 3,446,859 A * | 5/1969 | Weil et al. ............ | 570/159 |
| 3,502,734 A | 3/1970 | Baird et al. | |
| 3,558,438 A | 1/1971 | Schoenbeck | |
| 3,651,019 A | 3/1972 | Asscher | |
| 3,676,508 A | 7/1972 | Krekeler et al. | |
| 3,819,731 A * | 6/1974 | Pitt et al. ............ | 570/187 |
| 3,823,195 A | 7/1974 | Smith | |
| 3,872,664 A | 3/1975 | Lohmann et al. | |
| 3,914,167 A | 10/1975 | Ivy et al. | |
| 3,926,758 A | 12/1975 | Smith | |
| 3,948,858 A | 4/1976 | Weirsum | |
| 3,954,410 A | 5/1976 | Pohl | |
| 4,051,182 A | 9/1977 | Pitt | |
| 4,513,154 A | 4/1985 | Kurtz | |
| 4,535,194 A | 8/1985 | Woodard | |
| 4,614,572 A | 9/1986 | Holbrook | |
| 4,650,914 A | 3/1987 | Woodard | |
| 4,661,648 A | 4/1987 | Franklin | |
| 4,702,809 A | 10/1987 | Mueller | |
| 4,714,792 A | 12/1987 | Mueller et al. | |
| 4,716,255 A | 12/1987 | Mueller | |
| 4,726,686 A | 2/1988 | Wolf | |
| 4,727,181 A | 2/1988 | Kruper | |
| 4,894,205 A | 1/1990 | Westerman et al. | |
| 4,902,393 A | 2/1990 | Mueller | |
| 5,057,634 A | 10/1991 | Webster | |
| 5,132,473 A | 7/1992 | Furutaka et al. | |
| 5,171,899 A | 12/1992 | Furutaka et al. | |
| 5,254,771 A | 10/1993 | Cremer et al. | |
| 5,254,772 A | 10/1993 | Dukat | |
| 5,315,044 A | 5/1994 | Furutaka et al. | |
| 5,414,166 A | 5/1995 | Kim et al. | |
| 5,684,219 A | 11/1997 | Boyce | |
| 5,811,605 A | 9/1998 | Tang et al. | |
| 5,895,825 A | 4/1999 | Elsheikh et al. | |
| 5,986,151 A | 11/1999 | Van der Puy et al. | |
| 6,111,150 A | 8/2000 | Sakyu et al. | |
| 6,118,018 A | 9/2000 | Savidakis | |

(Continued)

FOREIGN PATENT DOCUMENTS

| | | |
|---|---|---|
| CH | 609022 A5 | 2/1979 |
| CN | 101492341 | 7/2009 |

(Continued)

OTHER PUBLICATIONS

Nikishin et al., "Reactions of Methanol and Ethanol with Tetrachloroethylene", N.D. Zelinskii Institute of Organic Chemistry, Academy of Sciences of the USSR, Translated from Izvestiya Akademii Nauk SSSR, Seriya Khimicheskaya, No. 12, pp. 2188-2192, Dec. 1966.
Kruper et al., "Synthesis of alpha Halocinnamate Esters via Solvolytic Rearrangement of Trichloroallyl Alcohols", J. Org. Chem, 1991, pp. 3323-3329, 1991.
PCT/US2010/051954 International Search Report, mailed Jun. 8, 2011.
Semenov et al., "Selectivity of Photochemical Chlorination of Chloromethane in the Liquid Phase", Viniti, 3405-84, Feb. 13, 1988.
International Search Report and Written Opinion, PCT/US2010/051954, mailed Jun. 8, 2011.

(Continued)

*Primary Examiner* — Sudhakar Katakam

(74) *Attorney, Agent, or Firm* — Lois K. Ruszala; KSJLaw, LLC

(57) ABSTRACT

The present invention provides one-step processes for the production of chlorinated and/or fluorinated propenes. The processes provide good product yield with low, e.g., less than about 20%, or even less than 10%, concentrations of residues/by-products. Advantageously, the processes may be conducted at low temperatures than 500° C. so that energy savings are provided, and/or at higher pressures so that high throughputs may also be realized. The use of catalysts or initiators may provide additional enhancements to conversion rates and selectivity, as may adjustments to the molar ratio of the reactants.

17 Claims, No Drawings

(56) References Cited

U.S. PATENT DOCUMENTS

| | | | |
|---|---|---|---|
| 6,160,187 A | 12/2000 | Strickler et al. |
| 6,187,976 B1 | 2/2001 | Van Der Puy et al. |
| 6,229,057 B1 | 5/2001 | Jackson et al. |
| 6,472,573 B1 | 10/2002 | Yamamoto |
| 6,545,176 B1 | 4/2003 | Tsay et al. |
| 6,551,469 B1 | 4/2003 | Nair et al. |
| 6,610,177 B2 | 8/2003 | Tsay et al. |
| 6,825,383 B1 | 11/2004 | Dewkar et al. |
| 6,958,135 B1 | 10/2005 | Filippi et al. |
| 7,117,934 B2 | 10/2006 | Lomax et al. |
| 7,189,884 B2 | 3/2007 | Mukhopadhyay et al. |
| 7,226,567 B1 | 6/2007 | Olbert et al. |
| 7,282,120 B2 | 10/2007 | Braun et al. |
| 7,297,814 B2 | 11/2007 | Yada |
| 7,345,209 B2 | 3/2008 | Mukhopadhyay et al. |
| 7,371,904 B2 | 5/2008 | Ma et al. |
| 7,378,559 B2 | 5/2008 | Verwijs et al. |
| 7,511,101 B2 | 3/2009 | Nguyen et al. |
| 7,521,029 B2 | 4/2009 | Guetlhuber et al. |
| 7,588,739 B2 | 9/2009 | Sugiyama et al. |
| 7,659,434 B2 | 2/2010 | Mukhopadhyay et al. |
| 7,674,939 B2 | 3/2010 | Mukhopadhyay et al. |
| 7,687,670 B2 | 3/2010 | Nappa |
| 7,695,695 B2 | 4/2010 | Shin |
| 7,714,177 B2 | 5/2010 | Mukhopadhyay et al. |
| 7,880,040 B2 | 2/2011 | Mukhopadhyay et al. |
| 7,951,982 B2 | 5/2011 | Mukhopadhyay et al. |
| 8,058,486 B2 | 11/2011 | Merkel et al. |
| 8,058,490 B2 | 11/2011 | Strebelle |
| 8,071,825 B2 | 12/2011 | Johnson |
| 8,115,038 B2 | 2/2012 | Wilson et al. |
| 8,123,398 B2 | 2/2012 | Teshima et al. |
| 8,158,836 B2 | 4/2012 | Pigamo et al. |
| 8,232,435 B2 | 7/2012 | Sievert |
| 2002/0110711 A1 | 8/2002 | Boneberg |
| 2005/0245773 A1 | 11/2005 | Mukhopadhyay |
| 2006/0150445 A1 | 7/2006 | Redding |
| 2006/0258891 A1 | 11/2006 | Mukhopadhyay et al. |
| 2006/0292046 A1 | 12/2006 | Fruchey |
| 2007/0112229 A1 | 5/2007 | Mukhopadhyay et al. |
| 2007/0197841 A1 | 8/2007 | Mukhopadhyay et al. |
| 2007/0197842 A1 | 8/2007 | Mukhopadhyay et al. |
| 2007/0265368 A1 | 11/2007 | Rao et al. |
| 2008/0021229 A1 | 1/2008 | Maughon et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0030249 A1 | 1/2009 | Merkel et al. |
| 2009/0099396 A1 | 4/2009 | Mukhopadhyay et al. |
| 2009/0117014 A1 | 5/2009 | Carpenter |
| 2009/0203945 A1 | 8/2009 | Mukhopadhyay et al. |
| 2009/0253946 A1* | 10/2009 | Van Der Puy ............ 570/159 |
| 2009/0306438 A1 | 12/2009 | Sievert et al. |
| 2010/0185029 A1 | 7/2010 | Elsheikh et al. |
| 2010/0210883 A1 | 8/2010 | Mukhopadhyay et al. |
| 2011/0083955 A1 | 4/2011 | Tirtowidjojo et al. |
| 2011/0172472 A1 | 7/2011 | Sakyu |
| 2011/0178343 A1 | 7/2011 | Kruper, Jr. |
| 2011/0218369 A1 | 9/2011 | Elsheikh et al. |
| 2011/0251442 A1 | 10/2011 | Okamoto |
| 2012/0035402 A1 | 2/2012 | Wilson et al. |
| 2012/0041239 A1 | 2/2012 | Suzuki |
| 2012/0065434 A1 | 3/2012 | Nose et al. |

FOREIGN PATENT DOCUMENTS

| | | |
|---|---|---|
| CN | 101544535 | 9/2009 |
| CN | 101913979 | 12/2010 |
| CN | 101913980 | 12/2010 |
| CN | 101955414 | 1/2011 |
| CN | 101955414 A | 1/2011 |
| CN | 101982227 | 3/2011 |
| CN | 102001911 | 4/2011 |
| CN | 102249846 | 11/2011 |
| CN | 102351637 A | 2/2012 |
| DE | 857955 | 12/1952 |
| DE | 209184 | 4/1984 |
| DE | 235631 | 5/1986 |
| EP | 0131560 A1 | 1/1985 |
| EP | 0164798 | 12/1985 |
| EP | 1018366 | 12/2000 |
| EP | 1018366 A2 | 12/2000 |
| GB | 471188 | 8/1937 |
| GB | 857086 | 12/1960 |
| GB | 1134585 | 11/1968 |
| GB | 1381619 | 1/1975 |
| JP | 54-079207 A | 6/1979 |
| JP | 2001151708 | 6/2001 |
| JP | 2001213820 | 8/2001 |
| JP | 2007021396 | 2/2007 |
| JP | 2007021396 A | 2/2007 |
| JP | 2008063314 | 3/2008 |
| JP | 2009046653 | 3/2009 |
| JP | 2011144148 | 7/2011 |
| LU | 52247 | 12/1966 |
| RU | 899523 | 1/1982 |
| SU | 899523 | 1/1982 |
| WO | 0138271 | 5/2001 |
| WO | 0138275 | 5/2001 |
| WO | 2007079431 | 7/2007 |
| WO | 2007079435 | 7/2007 |
| WO | 2009003084 A1 | 12/2008 |
| WO | 2009067571 | 5/2009 |
| WO | 2009087423 | 7/2009 |
| WO | 2011060211 | 5/2011 |
| WO | 2011065574 | 6/2011 |
| WO | 2012166393 | 12/2012 |

OTHER PUBLICATIONS

Boualy et al., "Kharasch addition of Tetrachloromethane to alkenes catalyzed by metal acetylacetonates", Catalysis Communications, 2011, 1295-1297, 12.

Cristiano et al., Tetraalkylphosphonium Trihalides. Room Temperature Ionic Liquids As Halogenation Reagents, J. Org. Chem., 2009, 9027-9033, 74.

Evstigneev et al., "Initiated Chlorination of Tetrachloropropane", Khim. Prom., 1984, 393-394,16:7.

Ivanov et al., "Metal phthalocyanine-catalyzed addition of polychlorine-containing organic compounds to C=C bonds," Russian Chemical Bulletin, International Edition, 2009, 2393-2396 58(11).

Kharasch et al., "Chlorinations with Sulfuryl Chloride.I. The Peroxide-Catalyzed Chlorination of Hydrocarbons", J. Am. Chem. Soc., 1939, 2142-2150, 61.

Munoz-Molina et al., "An Efficient, Selective and Reducing Agent-Free Copper Catalyst for the Atom-Transfer Radical Addition of Halo Compounds to Activated Olefins", Inorg. Chem., 2010, 643-645, 49.

Nair et al., "Atom transfer radical addition (ATRA) of carbon tetrachloride and chlorinated esters to various olefins catalyzed by CP/Ru(PPh3)(PR3)Cl complexes", Inorganica Chimica Acta, 2012, 96-103, 380.

Rotshtein et al., "Isomer Distribution on Chlorination of Chloropropanes", Z. Organicheskoi Khimii, 1966, 1539-1542, 2(9).

Semenov et al., "Selectivity of Photochemical Chlorination of Chloromethane in the Liquid Phase", Viniti, 1988, 3405-84.

Tanuma et al., "Partially Fluorinated Metal Oxide Catalysts for a Friedel-Crafts-type Reaction of Dichlorofluoromethane with Tetrafluoroethylene", Catal. Lett., 2010, 77-82, 136.

Ying et al., Isomerization of tetrachloropropene to promote utilization ration of triallate raw materials, Petrochemical Technology & Application, 2007, 25(1).

Zhao et al., "Research Progress on Preparation Technology of 1,1,2,3-Tetrachloropropene", Zhejiang Chemical Industry, vol. 41, No. 8 (2010).

Herzfelder, "Substitution in the Aliphatic Series", Berichte der Deutschen Chemischen Gesellschaft, 1893, 1257-1261, 26(II).

McBee et al., "Utilization of Polychloropropanes and Hexachloroethane", Industrial and Engineering Chemistry, Feb. 1941, 176-181, 33(2).

(56) References Cited

OTHER PUBLICATIONS

Mouneyrat, "Effect of chlorine on propyl chloride in the presence of anhydrous aluminum chloride", Bulletin de la Societe Chimique de Paris, Jan. 1899, 616-623, 3(21).
Chai et al., "Study of Preparation of 1,1,1,3-Tetrachloropane", Zhejiang Chemical Industry, 2010, pp. 1-3, 41(5).
Gault et al., "Sur la chloruatoin du chloroforme", Comptes Rendus Hebdomadaires des seances de L'Academie de Sciences, 1924, pp. 467-469, 179.
Gerding et al., "Raman Spectra of Aliphatic Chlorine Compounds II. Chloroethanes and chloropropanes", Recueil des travaux chimiques des pays bas, 1955, pp. 957-997.
Hatch et al., "Allylic Chlorides. XV. Preparation and Properties of the 1,2,3-Trichlooropropenes", JACS, Jan. 5, 1952, pp. 123-126, 74(1).
Hatch et al., "Allylic Chlorides. XVIII. Preparation and Properties of 1,1,3-Tricloro-2fluoro-1-propene and 1,1,2,3-Tetrachloro-1-propene", JACS, Jul. 5, 1952, pp. 3328-3330, 74(13).
Kang et al., "Kinetics of Synthesis of 1,1,1,3,3,-pentachlorobutane catalyzed by Fe—FeCl3", Huaue Yanjiu Yu, Yingyong, 2011, pp. 657-660, 23(6).
Khusnutdinov et al., "Addition of CCl4 to olefins catalyzed by complexes of chromium and ruthenium. Effect of water as a nucleophilic additive," Neftekhimiha, 2009, pp. 349-356, 49(4).
Leitch, "Organic Deuterium Compounds: V. The Chlorination of Propyne and Propyne-d4", Canadian Journal of Chemistry, Apr. 1, 1953, pp. 385-386, 31(4).
Levanova et al., "Thermocatalytic Reactions of Bromochloropropanes", Russian Journal of Physical Chemistry, Chemical Society, London, GB, Jan. 1, 1983, pp. 1142-1146 vol. 57.
Liu et al., "Progress in Synthesis of 1,1,1,3-tetrachloropropane", Guangzhou Huabonb (2011), pp. 41-42, 39(5).
Pozdnev et al., "Chlorination of Chloroform and the conversion of methylene chloride manufacture still residues", Khim. Khim. Tekhnol., 1970, pp. 70-74, 70(4).
Skell et al., "Selectivities of pi and sigma Succinimidyl Radicals in Substitution and Addition Reactions. Appendix: Response to Walling, El-Taliawi and Zhao", JACS, 1983, pp. 5125-5131, 105(1).
Skell et al., "Reactions of BrCl with Alkyl Radicals", Tetrahedron Letters, 1986, pp. 5181-5184, 27(43).
Urry et al., Free-Radical Reactions of Diazomethanewith Reactive Bromopolychloroakanes, JACS, May 5, 1964, pp. 1815-1819, 86(9).
Wang, "Elimination Reactions of Polyhalopropanes under Emulsion Catalytic Conditions to give Halopropenes", Synthesis, Georg Thieme Verlag, Stuttgart, DE, Jan. 1, 1982, pp. 494-496, 1982(6).
Zheng et al., "Preparation of the low GWP alternative 1,3,3,3-tetrafluoropropene", Zhejiang Huagong, 2010, pp. 5-7, 41(3).

* cited by examiner

PROCESS FOR THE PRODUCTION OF CHLORINATED AND/OR FLUORINATED PROPENES

FIELD

The present invention relates to processes for the production of chlorinated and/or fluorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser detrimental impact on the ozone layer and their generally lower GWP. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene (HFO-1234yf) or 1,3,3,3-tetrafluoroprop-1 -ene (HFO-1234ze), may typically be produced utilizing feedstocks of chlorocarbons or chlorofluorocarbons, and in particular, chlorinated and/or fluorinated propenes.

Unfortunately, these chlorinated and/or fluorinated propenes may have limited commercial availability, and/or may only be available at potentially prohibitively high cost, due at least in part to the complicated, multi-step processes typically utilized in their manufacture. Furthermore, although simplified, one-step processes have been developed for the manufacture of chlorinated and/or fluorinated propenes, these processes have limited commercial applicability due to their limited throughput. Whether multi-step or one-step, many of the conventional manufacturing processes for the production of chlorinated and/or fluorinated propenes may typically result in the formation of large quantities of reaction byproducts that must then be separated from the product and disposed of, typically at great expense, further limiting their commercial potential.

It would thus be desirable to provide improved processes for the production of chlorocarbon precursors useful in the synthesis of HFO's. More particularly, such processes would provide an improvement over the current state of the art if they were less costly not only in materials, but in time expenditure. Improvements in reaction productivity, selectivity and/or process throughput that could be provided without substantial detrimental impact on expense and/or safety concerns associated with the process would also provide commercial advantage.

BRIEF DESCRIPTION

The present invention provides efficient processes for the production of chlorinated and/or fluorinated propenes. Advantageously, the processes are one-step processes, thereby providing significant time, operating and capital cost savings over conventional multi-step processes for the production of these precursors for HFO' s. Further, the processes provide good product yield with low, e.g., less than about 20%, or even less than about 10%, yield of residues/by-products. The processes may be conducted at low temperatures relative to conventional processes, so that energy savings are provided, and/or at higher pressures so that high throughputs may be realized. The use of catalysts may provide enhancements to conversion rates and selectivity over those seen in conventional processes, as may the optimization of the molar ratio of the reactants.

More specifically, the processes comprise reacting a chloroethylene or a chlorofluoroethylene with a methane, chloromethane, fluoromethane, or chlorofluoromethane to provide the chlorinated and/or fluorinated propene. The chloroethylene or chlorofluoroethylene has the formula $CHCl=CX_2$, where each X is independently Cl or F, while the methane, chloromethane, fluoromethane or chloromethane may desirably have the formula $CH_{4-a-b}Cl_aF_b$, wherein a is 0-3 and b is 0-3 and 4-a-b is greater than 0. The chlorinated and/or fluorinated propene may, in some embodiments, have the formula $CCl_cF_{2-c}=CH-CH_{3-e-f}Cl_eF_f$ wherein c is 0-2, e is 0-3, and f is 0-3, and 3-e-f is greater than or equal to 0.

In some embodiments, the chloroethylene or chlorofluoroethylene may desirably be trichloroethylene, 1-chloro,2,2-difluoroethylene, cis-1,2-dichloro,2-fluoro ethylene, or trans-1,2-dichloro. Preferred methanes, chloromethanes, fluoromethanes or chlorofluoromethanes include methane, methyl fluoride, methyl chloride, methylene chloride, methyl difluoride, methyl trifluoride, chloromethane, dichloromethane, trichloromethane, fluoromethane, difluoromethane, trifluoromethane, chloroform chlorodifluoromethane, dichlorofluoromethane, and chlorofluoromethane.

Preferred chlorinated and/or fluorinated propenes produced by the present process include 1,1,3,3 -tetrafluoropropene, 1,1,3,3,3-pentafluoropropene, 1,1-dichloropropene 1,1,3-trichloropropene, 1,1,3,3,3-pentachloropropene, 1,1,3,3-tetrachloro,3-fluoropropene, 1,1,3-trichloro,3-fluoropropene, 1,1,3-trichloro-3,3-difluoropropene, 1,1-dichloro-3,3,3-trifluoropropene, 1,1-dichloro,3,3-difluoropropene, 1,1-dichloro,3-fluoropropene, cis/trans 1-chloro,1-fluoropropene, cis/trans 1,3 -dichloro,1-fluoropropene, 1,3,3 -trichloro-1,3 -difluoropropene, 1,3-dichloro-1,3,3-trifluoropropene, 1-chloro-1,3,3,3-tetrafluoropropene, 1-chloro,1,3,3-trifluoropropene, 1-chloro-1,3-difluoropropene, 1,1-difluoropropene, 3-chloro,1,1-difluoropropene, 3,3,-dichloro,1,1-difluoropropene, 3,3,3,-trichloro, 1,1,difluoropropene, 1,1,3-trifluoropropene, 1,1,3,3-tetrafluoropropene, 1,1,3,3,3-pentafluoropropene, 3-chloro,1,1,3-trifluoropropene, 3,3-dichloro,1,1,3-trifluoropropene, 3-chloro,1,1,3,3-tetrafluoropropene, cis/trans 1,3,3-trichloro,1-fluoropropene, cis/trans 1,3,3,3-tetrachloro,1-fluoropropene, cis/trans 1-chloro,1,3-difluoropropene, cis/trans 1-chloro-1,3,3-trifluoropropene, cis/trans 1-chloro,1,3,3,3-tetrafluoropropene, cis/trans 1,3-dichloro,1,3-difluoropropene, cis/trans 1,3,3-trichloro, 1,3-difluoropropene, cis/trans 1,3,-dichloro,1,3,3-trifluoropropene .

Desirably, the processes will be conducted at pressures of at least about 15 psig, or at least about 200 psig, or even at pressures of at least about 300 psig. The temperature of the processes may advantageously be lower than those utilized in conventional processes, i.e., the temperature may be less than about 500° C., or less than about 450° C. or even less than about 400° C. Catalysts may be utilized in the process, and in those embodiments where the same is desired, free radical initiators, such as those comprising chlorine, e.g., carbon tetrachloride (Tet), hexachloroethane (HCE), benzotrichloride (BTC), hexachloroacetone (HCA), chlorine, or combinations of these, may be utilized. The ratio of $CH_{4-a-b}Cl_aF_b$ to $CHCl=CX_2$ may advantageously be greater than 0.5, greater than 2.0, or greater than about 2.5. Combinations of one or more of elevated pressure, lower temperatures, the use of a catalyst, and the ratio of $CH_{4-a-b}Cl_aF_b$ to $CHCl=CX_2$ may be utilized to provide further enhancements to the conversion rate, selectivity and/or cost savings provided by the process.

The processes described herein are expected to provide particular benefit when utilized to produce chlorinated and/or fluorinated propenes or higher alkenes, and in another aspect, the present invention so provides. The advantages provided by the present processes may be carried forward by utilizing the chlorinated and/or fluorinated propenes or higher alkenes to produce further downstream products, such as, e.g., 1,3,3,3-tetrafluoroprop-1-ene (HFO-1234ze).

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to bely any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Further, "M2" may be used as an abbreviation for methylene chloride, and "Tric" may be used as an abbreviation for trichloroethylene. "Tet" may be used as an abbreviation for carbon tetrachloride, "BTC" may be used as an abbreviation for benzotrichloride, "HCE" may be used as an abbreviation for hexachloroethane, and "HCA" may be used as an abbreviation for hexachloroacetone. Throughout the specification, the formula $CHCl=CX_2$ wherein each X is independently Cl or F indicates the chloroethylene or chlorofluoroethylene, as the case may be, while the formula $CH_{4-a-b}Cl_aF_b$, wherein a is 0-3, b is 0-3 and 4-a-b is greater than 0 may be used to indicate the methane, chloromethane, fluoromethane or chlorofluoromethane. Finally, the formula $CCl_cF_{2-c}=CH—CH_{3-e-f}Cl_eF_f$ wherein c is 0-2, e is 0-3, and f is 0-3, and 3-e-f is greater than or equal to 0, respectively, means the chlorinated and/or fluorinated propene(s).

The present invention provides efficient processes for the production of chlorinated and/or fluorinated propenes. The present processes comprise only one step, the reaction of a chloroethylene or a chlorofluoroethylene with a methane, chloromethane, fluoromethane, or chlorofluoromethane, thus, providing a significant time and materials savings as compared to conventional processes. Additionally, the present processes may be carried out at lower temperatures than conventional processes, thus providing a cost savings, while yet also providing commercially acceptable throughputs not achieved by conventional high temperature processes.

Further, the present processes provide this good product yield while also providing low, e.g., less than about 20%, or even less than about 10% yield of residues/by-products. The use of catalysts may provide further enhancements e.g., to conversion rates and selectivity as may the optimization of the molar ratio of the reactants.

In additional embodiments, one or more reaction conditions of the one step process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Because of such improvements, the one-step process of the present invention may provide conversion rates of the methane, chloromethane, fluoromethane or chlorofluoromethane of at least about 2%, or about 5%, or about 10%, or up to about 10%, or in some instances, even up to about 50% or greater, without substantially reducing selectivity to the chlorinated and/or fluorinated propene. Conversion rates of chloroethylene or chlorofluoroethylene of at least about 5%, or at least about 10%, or at least about 15%, or even up to about 20% or better can be seen. Concentrations of impurities, such as redox impurities, of less than about 5 mole percent, less than about 2 mole percent, and in some embodiments, even less than 0.5 mole percent may also be provided. The present processes also surprisingly provide selectivities to the chlorinated and/or fluorinated propene of at least about 50%, or up to about 60%, up to about 70%, up to about 80% when chloroethylene or chlorofluoroethylene conversion is 30% or less, or up to about 90% when chloroethylene or chlorofluoroethylene conversion is 20% or less.

The chloroethylene or chlorofluoroethylene utilized in the present processes desirably have the formula $CHCl=CX_2$ where each X is independently Cl or F. Suitable chloroethylenes or chlorofluoroethylenes comprise a hydrogen atom. Exemplary chloroethylenes and chlorofluoroethylenes that may be utilized in the present process thus include trichloroethylene, 1-chloro,2,2-difluoroethylene, cis-1,2-dichloro,1-fluoro ethylene, trans-1,2-dichloro,1-fluoro ethylene, cis-1,2-dichloro,2-fluoro ethylene, trans-1,2-dichloro,2-fluoro ethylene, 1-chloro, 2,2-difluoro ethylene, or combinations of these.

The methane, chloromethane, fluoromethane or chlorofluoromethane utilized in the present processes desirably have the formula $CH_{4-a-b}Cl_aF_b$ wherein a and b are independently 0-3, and 4-a-b is greater than 0. Suitable chloromethanes, fluoromethanes and chlorofluoromethanes comprise at least one hydrogen atom. Thus, suitable methanes, chloromethanes, fluoromethanes and chloromethanes include methane, methyl fluoride, methyl chloride, methylene fluoride, methylene chloride, methyl difluoride, methyl trifluoride, chloromethane, dichloromethane, trichloromethane, fluoromethane, difluoromethane, trifluoromethane, chloroform, chlorodifluoromethane, di chloro fluoromethane, chlorofluoromethane, or combinations of these.

The present processes may advantageously be utilized to produce chlorinated and/or fluorinated propenes in one step. In some embodiments, the chlorinated and/or fluorinated propenes that can be produced according to the present process include those having the formula $CCl_cF_{2-c}=CH-CH_{3-e-f}Cl_eF_f$ wherein c is 0-2, e is 0-3, and f is 0-3. Examples of these include, for example, 1,1,3,3-tetrafluoropropene, 1,1-dichloropropene 1,1,3-trichloropropene, 1,1,3,3-tetrachloropropene, 1,1,3,3,3-pentachloropropene, 1,1,3,3-tetrachloro-3-fluoro-propene, 1,1,3-trichloro-3-fluoro-propene, 1,1,3-trichloro-3,3-difluoro-propene, 1,1-dichloro-3,3,3-trifluoro-propene, 1,1 -dichloro,3,3-difluoropropene, 1,1 -dichloro,3-fluoro-propene, cis/trans 1-chloro,1-fluoropropene, cis/trans 1,3-dichloro,1-fluoropropene, 1,3,3-trichloro,1-fluoropropene, 1,3,3,3-tetrachloro, 1-fluoropropene, 1,3,3-trichloro-1,3-difluoro-propene, 1,3-dichloro-1,3-difluoropropene, 1,3-dichloro-1,3,3-trifluoro-propene, 1-chloro-1,3,3,3-tetrafluoropropene, 1-chloro,1,3,3-trifluoropropene, 1-chloro-1,3-difluoropropene, 1,1-difluoropropene, 3-chloro,1,1-difluoropropene, 3,3,-dichloro,1,1-difluoropropene, 3,3,3,-trichloro, 1,1,-difluoropropene, 1,3-trifluoropropene, 1,1,3,3-tetrafluoropropene, 1,1,3,3,3-pentafluoropropene, 3-chloro,1,1,3-triuoropropene, 3,3-dichloro,1,1,3-trifluoropropene, 3-chloro,1,1,3,3-tetrafluoropropene, cis/trans 1,3,3-trichloro,1-fluoropropene, cis/trans 1,3,3,3-tetrachloro,1-fluoropropene, cis/trans 1 -chloro, 1,3-difluoropropene, cis/trans 1-chloro,1,3,3-trifluoropropene, cis/trans 1-chloro,1,3,3,3-tetrafluoropropene, cis/trans 1,3-dichloro,1,3-difluoropropene , cis/trans 1,3,3-trichloro, 1,3-difluoropropene, cis/trans 1,3,-dichloro,1,3,3-trifluoropropene, or combinations of these.

For example, in some embodiments wherein the chloroethylene comprises trichloroethylene, the methane, chloromethane, fluoromethane or chlorofluoromethane, may comprise methyl chloride, methylene chloride, chloroform, methane, methyl fluoride, methyl difluoride, methyl trifluoride, chlorofluoromethane, chlorodifluoromethane, and/or dichlorofluoromethane and the chlorinated and/or fluorinated propene may comprise 1,1,3-trichloropropene, 1,1-dichloro, 3,3-difluoropropene, 1,1,3,3,3-pentachloropropene, 1,1-dichloropropene, 1,1-dichloro,3-fluoropropene, 1,1-dichloro,3,3-difluoropropene, 1,1-dichloro, 3,3,3-trifluoropropene, 1,1,3-trichloro, 3-fluoropropene, 1,1,3-trichloro, 3,3-difluoropropene, and/or 1,1,3,3-tetrachloro, 3-fluoropropene, respectively.

In other embodiments wherein the chloroethylene or chlorofluoroethylene comprises 1-chloro,2,2-difluoroethylene, the methane, chloromethane, fluoromethane or chlorofluoromethane, may comprise methane, chloromethane, dichloromethane, trichloromethane, fluoromethane, difluoromethane, trifluoromethane, chlorofluoromethane, dichlorofluoromethane, and/or chlorodifluoromethane and the chlorinated and/or fluorinated propene may comprise 1,1-difluoropropene, 3-chloro,1,1-difluoropropene, 3,3-dichloro, 1,1-difluoropropene, 3,3,3-trichloro,1,1-difluoropropene, 1,1,3-trifluoropropene, 1,1,3,3-tetrafluoropropene, 1,1,3,3,3-pentafluoropropene, 3-chloro,1,1,3-trifluoropropene, 3,3-dichloro,1,1,3-trifluoropropene, and/or 3-chloro,1,1,3,3-tetrafluoropropene, respectively.

In yet other embodiments wherein the chloroethylene or chlorofluoroethylene comprises cis1,2-dichloro,2-fluoroethylene or trans1,2-dichloro,2-fluoroethylene the methane, chloromethane, fluoromethane or chlorofluoromethane, may comprise methane, chloromethane, dichloromethane, trichloromethane, fluoromethane, difluoromethane, trifluoromethane, chlorofluoromethane, dichlorofluoromethane and/or chlorodifluoromethane and the chlorinated and/or fluorinated propene may comprise cis/trans-1-chloro,1,fluoropropene, cis/trans-1,3-dichloro,1, fluoro-propene, cis/trans-1,3,3-trichloro,1,fluoro-propene comprises cis/trans-1,3,3,3-tetrachloro,1-fluoro-propene, cis/trans-1-chloro,1,3-difluoropropene, cis/trans-1-chloro,1,3,3-trifluoropropene, cis/trans-1-chloro,1,3,3,3-tetrafluoropropene, cis/trans-1,3-dichloro,1,3-difluoropropene, cis/trans-1,3,3-trichloro,1,3-difluoropropene, and/or cis/trans-1,3-dichloro,1,3,3-trifluoropropene, respectively.

Reaction conditions of the one-step process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, use of catalysts or initiators, etc.

In one embodiment, reaction pressure is advantageously optimized, and may provide enhanced chlorinated and/or fluorinated propene selectivities, than those carried out at ambient or lower pressures. More specifically, improvements to at least the chlorinated and/or fluorinated propene selectivity are expected at pressures of greater than about 15 psig, or greater than about 20 psig, or greater than about 35 psig, with improvement expected to increase with increase of pressure, up to about 200 psig, or up to about 300 psig, or up to about 400 psig, or even up to about 500 psig and greater. Optimizing at least pressure of the reaction in this fashion is estimated to provide chlorinated and/or fluorinated propene selectivity of at least about 50%, or up to about 60%, up to about 70%, and in some embodiments, up to about 80%. In other embodiments, the present processes may be carried out at ambient pressure.

The temperature of the reaction may also be optimized, and surprising results are expected when lowering the temperature, in particular when done in combination with pressure optimization. That is, although conventional processes typically call for temperatures of at least about 550° C., the present process may be carried out at less than 500° C., or less than about 450° C., or less than about 400° C., or less than about 350° C. or even lower, while yet providing improvements to reactant conversions, product selectivity and lowering the capital cost associated with the use of the reactor.

The molar ratio of the reactants may also be optimized. While a 1:1 ratio of $CH_{4-a-b}Cl_aF_b$ to $CHCl=CX_2$ or lower ratio may be used, provision of a stoichiometric excess of $CH_{4-a-b}Cl_aF_b$ may provide enhancements to the present process. More particularly, any molar ratio of $CH_{4-a-b}Cl_aF_b/CHCl=CX_2$ in which $CH_{4-a-b}Cl_aF_b$ is present in excess may be utilized that is expected to result in enhancements to the process, whether in the form of increases to conversion or selectivity, or decreases in the production of impurities. Molar ratios of greater than about 1:1, or greater than about 2.0, or greater than 2.5, or even greater than 5:1, may provide at least incremental improvements to the process. As with enhancements to temperature, any adjustments to the molar ratio may provide synergistic effects, but at least combinatorial enhancements, when utilized in conjunction with increases in reaction pressure.

Catalysts or initiators may also be utilized to enhance the present process. Surprisingly, the utilization of the same, in particular in conjunction with any of the other condition optimizations, does not result in an increase in the production of redox impurities by the process, but does provide selectivities to the chlorinated and/or fluorinated propene of at least about of at least about 50%, or up to about 60%, up to about 70%, and in some embodiments, up to about 80% or even higher.

Any catalyst or initiator capable of at least marginally enhancing the selectivity of the inventive process for the chlorinated and/or fluorinated propene may be utilized by itself or in a combination with others. Catalysts/initiators capable of doing so are believed to include those that are capable of removing hydrogen from methane, chloromethanes, fluoromethanes or chlorofluoromethanes to produce the corresponding radical. For example in the case of methyl chloride, the catalyst/initiators are capable for removing hydrogen from methyl chloride to form a chloromethyl radical, e.g., *$CH_2Cl$. Such free radical initiators are well known to those skilled in the art and have been reviewed, e.g., in "Aspects of some initiation and propagation processes," Bamford, Clement H. Univ. Liverpool, Liverpool, UK., Pure and Applied Chemistry, (1967), 15(3-4),333-48 and Sheppard, C. S.; Mageli, O. L. "Peroxides and peroxy compounds, organic," Kirk-Othmer Encycl. Chem. Technol., 3rd Ed. (1982), 17, 27-90, both of which are hereby incorporated herein by reference in their entirety for any and all purposes.

Such catalysts may typically comprise one or more chlorine or peroxide groups and/or exhibit reactor phase mobility/ activity. As used herein, the phrase "reactor phase mobility/ activity" means that a substantial amount of the catalyst or initiator is available for generating free radicals of sufficient energy which can initiate and propagate effective turnover of the product, chlorinated and/or fluorinated propene, within the design limitations of the reactor.

Examples of suitable catalysts/initiators comprising chlorine include, but are not limited to carbon tetrachloride, hexachloroacetone, chlorine, chloroform, hexachloroethane, phosgene, thionyl chloride, sulfuryl chloride, trichloromethylbenzene, perchlorinated alkylaryl functional groups, or organic and inorganic hypochlorites, including hypochlorous acid, and t-butylhypochlorite, methylhypochlorite, chlorinated amines (chloramine) and chlorinated amides or sulfonamides such as chloroamine-T200 , and the like. Combinations of any of these may also be utilized.

Carbon tetrachloride ($CCl_4$) and chlorine gas ($Cl_2$) are but two examples that are readily commercially available and easily integrated into the present process, and their use can be preferred in embodiments wherein the use of a catalyst or initiator is desired.

Examples of suitable catalysts/initiators comprising one or more peroxide groups include hydrogen peroxide, hypochlorous acid, aliphatic and aromatic peroxides or hydroperoxides, including di-t-butyl peroxide, benzoyl peroxide, cumyl peroxide and the like.

In addition bis-azo initiators may have utility in effecting the addition of $CH_{4-a-b}Cl_aF_b$ to $CHCl=CX_2$ under the conditions of this invention.

In general, the catalyst/initiator should have sufficient homolytic dissociation energies such that the theoretical maximum of free radicals is generated from a given initiator under the temperature/residence time of the process. It is especially useful to use free radical initiators at concentrations where free radical chlorination of incipient radicals is prevented due to low concentration or reactivity. Diperoxides offer an advantage of not being able to propagate competitive processes (e.g., the free radical chlorination of methylene chloride to chloroform and carbon tetrachloride).

Whatever the desired catalyst or initiator, those of ordinary skill in the art are well aware of methods of determining the appropriate concentration and method of introduction thereof. For example, many catalysts/initiators are typically introduced into the reactor zone as a separate feed, or in solution with other reactants, e.g., $CHCl=CX_2$, which can be evaporated prior to the reaction zone. Also, initiators with a low boiling point can be introduced with inert gaseous diluents such as $N_2$.

The amount of any catalyst or initiator utilized will depend upon the particular catalyst/initiator chosen as well as the other reaction conditions. Generally speaking, in those embodiments of the invention wherein the utilization of a catalyst/initiator is desired, enough of the catalyst/initiator should be utilized to provide some improvement to reaction process conditions (e.g., a reduction in required temperature) or realized products, but yet not be more than will provide any additional benefit, if only for reasons of economic practicality. For purposes of illustration only, then, it is expected in those embodiments wherein a catalyst or initiator comprising carbon tetrachloride is desirably utilized, that useful concentrations thereof will range from about 5 ppm to about 200000 ppm, or from about 10 ppm to about 100000 ppm, or from about 20 ppm to about 50000 ppm, inclusive of all subranges therebetween.

The process can be further enhanced by subjecting the process or reactor zone to pulse laser or continuous UV/visible light sources at a wavelength suitable for inducing photolysis of the radical catalyst/initiator, as taught by Breslow, R. in *Organic Reaction Mechanisms* W. A. Benjamin Pub, New York p 223-224, hereby incorporated by reference herein in its entirety for any and all purposes. Wavelengths from about 300 to 700 nm of the light source are sufficient to dissociate commercially available radical initiators. Such light sources include, .e.g, Hanovia UV discharge lamps, sunlamps or even pulsed laser beams of appropriate wavelength or energy which are configured to irradiate the reactor chamber. Alternatively, chloromethyl radicals may be generated from microwave discharge into a bromochloromethane feedsource introduced to the reactor as taught by Bailleux et al., in Journal of Molecular Spectroscopy, 2005, vol. 229, pp. 140-144, hereby incorporated by reference herein in its entirety for any and all purposes.

As mentioned above, the present invention provides economical processes for the production of chlorinated and/or fluorinated propenes, i.e., wherein one or more of the reaction conditions are optimized. In certain preferred embodiments, a lower temperature is utilized in conjunction with an increased pressure to provide a process that results in a product stream with lower amounts of impurities. Operating at much higher temperatures can suffer from excessive secondary decomposition of the desired chlorinated and/or fluorinated propene, which for some, is substantial at temperatures >400° C., lowering selectivity and process yield.

Even at short reactor contact times, 1,1,3,3-tetrachloropropene is unstable at 400° C.-500° C. and especially unstable at reaction temperatures greater than 500° C. The ensuing undesired reactions and/or decompositions lead to high concentrations of impurities, and ultimately thermal coking at these higher temperatures. For continuously fed, industrial reactors, coking is well known to cause further loss of reactor production capacity with time and often requires shutting down a reactor for cleaning and maintenance. Although the present invention is not so limited, reactions to produce 1,1,3,3-tetrachloropropene, as well as other similar reactions comprising reactants, products, diluents or byproducts with similar thermal sensitivity, are examples of those that can find particular benefit from application of the principles disclosed herein.

By running at temperatures lower than 500° C. not only are process cost savings provided, but lower capital costs are associated with the use of the reactor. And yet, in these embodiments of the invention, $CHCl=CX_2$ conversions of at least about 5%, or at least about 10%, or at least about 15%, or even up to about 20% or even greater can be seen, along with $CH_{4-a-b}Cl_aF_b$ conversions of at least about 2%, or about 5%, or about 10%, or up to about 20%, or in some instances, even up to about 40% or greater and chlorinated and/or fluorinated propene selectivities of at least about 50%, or up to about 60%, up to about 70%, up to about 80% when $CHCl=CX_2$ conversion is 30% or less, or up to about 90% when $CHCl=CX_2$ conversion is 20% or less.

In an additional particularly preferred embodiment, higher pressure, i.e., greater than ambient, may be utilized in combination with an increased $CH_{4-a-b}Cl_aF_b/CHCl=CX_2$ ratio (i.e., greater than 1), a lowered temperature (i.e., lower than about 500° C.) and a catalyst/initiator to provide a process for the production of chlorinated and/or fluorinated propenes with expected $CHCl=CX_2$ conversions of at least about 5%, or even 10%, as well as chlorinated and/or fluorinated propene selectivities of at least about 75%, or even 80%, 85%, or even up to 95% or greater. One particular such embodiment may utilize a reaction pressure of at least about 200 psig, or about 300 psig, or about 400 psig, a reaction temperature of lower than about 500° C., or lower than about 450° C., or even lower than about 400° C., a molar ratio of $CH_{4-a-b}Cl_aF_b/CHCl=CX_2$ of greater than about 0.5, or greater than about 2.0, or greater than about 2.5, and a catalyst/initiator, e.g., such as those comprising chlorine, including but not limited to, chlorine gas, carbon tetrachloromethane, or hexachloroethane or combinations of these, in a concentration of from about 5 ppm to about 200000 ppm, or from about 10 ppm to about 100000 ppm, or lower depending on the efficiency of the initiator.

Surprisingly, the gas phase conditions described herein for the production of chlorinated and/or fluorinated propenes from the reaction of methane, chloromethanes, fluoromethanes or chlorofluoromethanes having the formula $CH_{4-a-b}Cl_aF_b$ wherein a and b are independently from 0-3 and chloroethylene or chlorofluoroethylenes having the formula $CHCl=CX_2$ wherein each X is independently Cl or F show a preferred regioselectivity for the 1,1,3,3-tetrachloropropene isomer with little to no formation of the other possible isomer cis-1, 2,3,3-tetrachloropropene or trans-1,2,3,3-tetrachloropropene. The substantial absence of this unwanted isomer allows for greater selectivity in the downstream production of HFO-1234-ze.

A further unexpected element in the addition of $CH_{4-a-b}Cl_aF_b$ to $CHCl=CX_2$ in a continuous, gas phase process is the ability to chain carry the radical process at very low temperatures. The added elements of optimized $CH_{4-a-b}Cl_aF_b/CHCl=CX_2$ ratios and use of high pressure and appropriate radical initiators has allowed for substantial $CHCl=CX_2$ conversion at temperatures as low as 370° C. Even with short residence contact times in a continuous process, the thermal instability of certain chlorinated and/or fluorinated propenes can lead to the formation of by-products and coke, thereby limiting reactor throughput. Higher selectivity afforded at these even lower temperatures is a significantly added process benefit giving a lower energy footprint and less reactor downtime which is normally required for decoking. Lower operating temperatures further enhance the lifetime of reactor materials of construction, thereby allowing for better capital economy.

The present process may be conducted in any suitable reactor. Desirably, the reactor utilized will be one wherein the reaction conditions are readily and easily altered as desired, and also, that can function without damage or fouling at the selected conditions. These are expected to include near-isothermal shells and multitube reactors where the desired temperature can be achieved by means of utilization of a heat transfer field. Adiabatic cylindrical or tube reactors may also be used, and if used can have any desired length to diameter aspect ratio so long as preheating to the desired reaction temperature is possible. If an adiabatic reactor is utilized, a larger $CH_{4-a-b}Cl_aF_b/CHCl=CX_2$ ratio, e.g., 10 or greater, or with the addition of a suitable diluents, such as inert diluents or $CH_{4-a-b}Cl_aF_b$ may be used in order to limit the adiabatic temperature rise, i.e., increase in temperature of less than 50° C., preferably from about 10° C. to about 20° C. Alternatively, a series of adiabatic reactors with at least one intercooler operatively disposed relative thereto can also be employed to obtain the desired overall conversion while maintaining the desired temperature rise within each reactor.

The chlorinated and/or fluorinated propenes produced by the present process may typically be processed to provide further downstream products including hydrofluoroolefins, such as, for example, 1,3,3,3-tetrafluoroprop-1-ene (HFO -1234ze). Since the present invention provides an improved process for the production of chlorinated and/or fluorinated propenes, it is contemplated that the improvements provided will carry forward to provide improvements to these downstream processes and/or products. Improved methods for the production of hydrofluoroolefins 1,3,3,3-tetrafluoroprop-1-ene (HFO -1234ze), are thus also provided herein.

The conversion of chlorinated and/or fluorinated propenes to provide hydrofluoroolefins may broadly comprise a single reaction or two or more reactions involving fluorination of a compound of the formula $C(X)_mCCl(Y)_n(C)(X)_m$ to at least one compound of the formula $CF_3CF=CHZ$, where each X, Y and Z is independently H, F, Cl, I or Br, and each m is independently 1, 2 or 3 and n is 0 or 1. A more specific example might involve a multi-step process wherein a feedstock of a chlorinated and/or fluorinated propene is fluorinated in a catalyzed, gas phase reaction to form a compound such as 1-chloro-3,3,3-trifluoropropene (1233 zd). The 1-chloro-2,3,3,3-tetrafluoropropane is then dehydrochlorinated to 1,3,3,3-tetrafluoropropene (1234ze) via a catalyzed, gas phase reaction.

The following examples are set forth for the purpose of illustrating the invention; but these examples are not intended to limit the invention in any manner. One skilled in the art will recognize a variety of substitutions and modifications of the examples that will fall within the scope of the invention. Particularly, even though the present description and examples refer with specificity to the reaction of $CH_{4-a-b}Cl_aF_b$ with $CHCl=CX_2$, the teachings herein, and advantages provided thereby, are expected to be readily and easily extrapolated by those of ordinary skill in the art to any free radical type reaction desirably conducted in the gas phase, and desirably employing chlorine radical catalyst/initiators.

EXAMPLE I

Use of Method to Produce
1,1,3,3-tetrachloropropene from Methylene Chloride
and Trichloroethylene

EXAMPLE IA

A flow of trichloroethylene (17 sccm), methylene chloride (42 sccm), and nitrogen (50 sccm) is established through an empty quartz tube (150 cc) maintained at 470° C. and at atmospheric pressure (15 psia). The retention time of the reaction mixture is about 30 seconds. The reactor effluent is passed through a water cooled condenser (70 cc) and collected in a cold trap (−78° C.). The mixture is warmed to room temperature to allow the produced hydrogen chloride to vent to a caustic scrubber. A light colored crude liquid is recovered from the trap and a representative portion is taken for analysis by gas chromatography and 1H NMR spectroscopy. trichloroethylene conversion, calculated as (mol % trichloroethylene based products/(mol % trichloroethylene based products+mol % trichloroethylene)), was 6.2%. 1,1,3,3-tetrachloropropene selectivity, calculated as (mol % 1,1,3,3-tetrachloropropene/mol % trichloroethylene based products) was 89%.

EXAMPLE IB

A flow of trichloroethylene (16 sccm), methylene chloride (40 sccm), benzotrichloride (1.2 sccm), and nitrogen (50 sccm) is established through an empty quartz tube (150 cc) maintained at 470° C. and at atmospheric pressure (15 psia). The retention time of the reaction mixture is about 30 seconds. The reactor effluent is passed through a water cooled condenser (70 cc) and collected in a cold trap (−78° C.). The mixture is warmed to room temperature to allow the produced hydrogen chloride to vent to a caustic scrubber. A light colored crude liquid is recovered from the trap and a representative portion is taken for analysis by gas chromatography and 1H NMR spectroscopy. Trichloroethylene conversion, calculated as (mol % trichloroethylene based products/(mol % trichloroethylene based products+mol % trichloroethylene)), was 10.1%. 1,1,3,3-tetrachloropropene selectivity, calculated as (mol % 1,1,3,3-tetrachloropropene/mol % trichloroethylene based products) was 89%.

EXAMPLE IC

A flow of trichloroethylene (139 sccm), methylene chloride (351 sccm), and nitrogen (300 sccm) is established through a Hastelloy C tube reactor (0.62" inner diameter, 10" in length) with two heated zones. Zone 1 (99 cc) represents the preheat zone and is typically kept at 300° C. and zone 2 (50 cc) is kept at the 385° C. The effluent is delivered to a room temperature steel vessel (2 L) while maintaining pressure (275 psia) and allowing the nitrogen and produced hydrogen chloride to vent to a caustic scrubber. The pressure is slowly reduced on the steel vessel and the remaining liquids are collected, passed through a 1 μm filter, and analyzed by gas chromatography and 1H NMR spectroscopy for quantitation.

Initially, the temperature within the reaction zone is adjusted to achieve near isothermal conditions of about 385° C. The flow is adjusted to provide a molar ratio of methylene chloride/trichloroethylene of about 2.5. At 30 second overall residence time, trichloroethylene conversion, calculated as (mol % trichloroethylene based products/(mol % trichloroethylene based products+mol % trichloroethylene)), was 7.7%. 1,1,3,3-tetrachloropropene selectivity, calculated as (mol % 1,1,3,3-tetrachloropropene/mol % trichloroethylene based products) was 93%.

EXAMPLE ID

A flow of trichloroethylene (120 sccm), methylene chloride (383 sccm), carbon tetrachloride (5.2 sccm) and nitrogen (280 sccm) is established through a Hastelloy C tube reactor (0.62" inner diameter, 10" in length) with two heated zones. Zone 1 (99 cc) represents the preheat zone and is typically kept at 300° C. and zone 2 (50 cc) is kept at the 385° C. The effluent is delivered to a room temperature steel vessel (2 L) while maintaining pressure (275 psia) and allowing the nitrogen and produced hydrogen chloride to vent to a caustic scrubber. The pressure is slowly reduced on the steel vessel and the remaining liquids are collected, passed through a 1 μm filter, and analyzed by gas chromatography and 1H NMR spectroscopy for quantitation.

Initially, the temperature within the reaction zone is adjusted to achieve near isothermal conditions of about 385° C. The flow is adjusted to provide a molar ratio of methylene chloride/trichloroethylene of about 2.5. At 30 second overall residence time, trichloroethylene conversion, calculated as (mol % trichloroethylene based products/(mol % trichloroethylene based products+mol % trichloroethylene)), was 8.0%. 1,1,3,3-tetrachloropropene selectivity, calculated as (mol % 1,1,3,3-tetrachloropropene/mol % trichloroethylene based products) was 92%.

EXAMPLE IE

A flow of trichloroethylene (115 sccm), methylene chloride (377 sccm), chlorine (5.0), and nitrogen (275 sccm) is established through a Hastelloy C tube reactor (0.62" inner diameter, 10" in length) with two heated zones. Zone 1 (99 cc) represents the preheat zone and is typically kept at 300° C. and zone 2 (50 cc) is kept at the 385° C. The effluent is delivered to a room temperature steel vessel (2 L) while maintaining pressure (275 psia) and allowing the nitrogen and produced hydrogen chloride to vent to a caustic scrubber. The pressure is slowly reduced on the steel vessel and the remaining liquids are collected, passed through a 1 μm filter, and analyzed by gas chromatography and 1H NMR spectroscopy for quantitation.

Initially, the temperature within the reaction zone is adjusted to achieve near isothermal conditions of about 385° C. The flow is adjusted to provide a molar ratio of methylene chloride/trichloroethylene of about 2.5. At 30 second overall residence time, trichloroethylene conversion, calculated as (mol % trichloroethylene based products/(mol % trichloroethylene based products+mol % trichloroethylene)), was 10.1%. 1,1,3,3-tetrachloropropene selectivity, calculated as (mol % 1,1,3,3-tetrachloropropene/mol % trichloroethylene based products) was 91%.

EXAMPLE IF

A flow of trichloroethylene (116 sccm), methylene chloride (381 sccm), benzotrichloride (6.3), and nitrogen (280 sccm) is established through a Hastelloy C tube reactor (0.62" inner diameter, 10" in length) with two heated zones. Zone 1 (99 cc) represents the preheat zone and is typically kept at 300° C. and zone 2 (50 cc) is kept at the 385° C. The effluent is delivered to a room temperature steel vessel (2 L) while maintaining pressure (275 psia) and allowing the nitrogen and produced hydrogen chloride to vent to a caustic scrubber. The pressure is slowly reduced on the steel vessel and the remaining liquids are collected, passed through a 1 μm filter, and analyzed by gas chromatography and 1H NMR spectroscopy for quantitation.

Initially, the temperature within the reaction zone is adjusted to achieve near isothermal conditions of about 385° C. The flow is adjusted to provide a molar ratio of methylene chloride/trichloroethylene of about 2.5. At 30 second overall residence time, trichloroethylene conversion, calculated as (mol % trichloroethylene based products/(mol % trichloroethylene based product +mol % trichloroethylene)), was 12.4%. 1,1,3,3-tetrachloropropene selectivity, calculated as (mol % 1,1,3,3-tetrachloropropene/mol % trichloroethylene based products) was 94%.

EXAMPLE IG

A flow of trichloroethylene (135 sccm), methylene chloride (351 sccm), hexachloroacetone (1.8), and nitrogen (280 sccm) is established through a Hastelloy C tube reactor (0.62" inner diameter, 10" in length) with two heated zones. Zone 1 (99 cc) represents the preheat zone and is typically kept at 300° C. and zone 2 (50 cc) is kept at the 385° C. The effluent is delivered to a room temperature steel vessel (2 L) while maintaining pressure (275 psia) and allowing the nitrogen and produced hydrogen chloride to vent to a caustic scrubber. The pressure is slowly reduced on the steel vessel and the remaining liquids are collected, passed through a 1 μm filter, and analyzed by gas chromatography and 1H NMR spectroscopy for quantitation.

Initially, the temperature within the reaction zone is adjusted to achieve near isothermal conditions of about 385° C. The flow is adjusted to provide a molar ratio of methylene chloride/trichloroethylene of about 2.5. At 30 second overall residence time, trichloroethylene conversion, calculated as (mol % trichloroethylene based products/(mol % trichloroethylene based products+mol % trichloroethylene)), was 17.5%. 1,1,3,3-tetrachloropropene selectivity, calculated as (mol % 1,1,3,3-tetrachloropropene/mol % trichloroethylene based products) was 93%.

EXAMPLE IH

A flow of trichloroethylene (275 sccm), methylene chloride (712 sccm), hexachloroacetone (3.7), and nitrogen (200 sccm) is established through a Hastelloy C tube reactor (0.62" inner diameter, 10" in length) with two heated zones. Zone 1 (99 cc) represents the preheat zone and is typically kept at 300° C. and zone 2 (50 cc) is kept at the 370° C. The effluent is delivered to a room temperature steel vessel (2 L) while maintaining pressure (415 psia) and allowing the nitrogen and produced hydrogen chloride to vent to a caustic scrubber. The pressure is slowly reduced on the steel vessel and the remaining liquids are collected, passed through a 1 μm filter, and analyzed by gas chromatography and 1H NMR spectroscopy for quantitation.

Initially, the temperature within the reaction zone is adjusted to achieve near isothermal conditions of about 370° C. The flow is adjusted to provide a molar ratio of methylene chloride/trichloroethylene of about 2.5. At 30 second overall residence time, trichloroethylene conversion, calculated as (mol % trichloroethylene based products/(mol % trichloroethylene based products+mol % trichloroethylene)), was 18.9%. 1,1,3,3-tetrachloropropene selectivity, calculated as (mol % 1,1,3,3-tetrachloropropene/mol % trichloroethylene based products) was 91%.

The results from Example I are summarized in Table 1, below.

TABLE 1

| ID | Temp (° C.) | Press (psia) | Res Time (s) | M2:Tric | Init. | Init. mol % | % Tric Conv. | % 1,1,3,3 Select. |
|---|---|---|---|---|---|---|---|---|
| Ex1A | 470 | 15 | 30 | 2.5 | None | — | 6.2 | 89 |
| Ex1B | 470 | 15 | 30 | 2.5 | BTC | 1.0 | 10.1 | 89 |
| Ex1C | 385 | 260 | 30 | 2.5 | None | — | 7.7 | 93 |
| Ex1D | 385 | 260 | 30 | 2.5 | Tet | 0.7 | 8.0 | 92 |
| Ex1E | 385 | 260 | 30 | 2.5 | Cl2 | 0.7 | 10.1 | 91 |
| Ex1F | 385 | 260 | 30 | 2.5 | BTC | 0.7 | 12.4 | 94 |
| Ex1G | 385 | 260 | 30 | 2.5 | HCA | 0.2 | 17.5 | 93 |
| Ex1H | 370 | 400 | 30 | 2.5 | HCA | 0.3 | 18.9 | 91 |

EXAMPLE II

Use Of Method To Produce Chlorinated And/Or Fluorinated Propenes From $CH_{4-a-b}Cl_aF_b$ and $CHCl=CX_2$ For the following examples, the protocol described above in connection with examples 1A-1H is followed generally.

More specifically, a flow of the compound according to the formula $CHCl=CX_2$ (17 sccm), the compound according to the formula $CH_{4-a-b}Cl_aF_b$ (42 sccm) specified in Table 2, below, and nitrogen (50 sccm) is established through an empty Inconel600 tube (150 cc) maintained at from about 350° C. to about 550° C. and at a pressure of from about 15 psia to about 600 psia. The retention time of the reaction mixture is about 30 seconds. The reactor effluent is passed through a water cooled condenser (70 cc) and collected in a cold trap (−78° C.). The mixture is warmed to room temperature to allow the produced hydrogen chloride to vent to a caustic scrubber. A light colored crude liquid is recovered from the trap and a representative portion is taken for analysis by gas chromatography and 1H NMR spectroscopy.

Initially, the temperature within the reaction zone is adjusted to achieve near isothermal conditions at the temperature shown in Table 2. The flow is adjusted to provide the molar ratio of $CH_{4-a-b}Cl_aF_b/CHCl=CX_2$ shown in Table 2. At 30 second overall residence time, conversion, calculated as (mol % $CHCl=CX_2$ based product/(mol % $CHCl=CX_2$ based product+mol % $CHCl=CX_2$)), is about 12%±5%. Product selectivity, calculated as (mol % product/mol % $CHCl=CX_2$ based products) is at least 50%, or up to about 60%, up to about 70%, and in some embodiments, up to about 80, or even up to about 90%,±5%.

The results from Example II are summarized in Table 2, below.

TABLE 2

| ID | CHCl=CX$_2$ | CH$_{4-a-b}$Cl$_a$F$_b$ | Temp (° C.) | Press (psia) | CH$_{4-a-b}$Cl$_a$F$_b$ : CHCl=CX$_2$ | Chlorinated and/or fluorinated propene |
|---|---|---|---|---|---|---|
| Ex2A | trichloroethylene | methyl chloride | 550 | — | 1:1 | 1,1,3-trichloropropene |
| Ex2B | trichloroethylene | methylene chloride | 525 | 15 | 1.5:1 | 1,1,3,3-tetrachloropropene |
| Ex2C | trichloroethylene | chloroform | 500 | 35 | 2:1 | 1,1,3,3-pentachloropropene |
| Ex2D | trichloroethylene | methane | 475 | 50 | 2.5:1 | 1,1-dichloropropene |
| Ex2E | trichloroethylene | methyl flouride | 450 | 100 | 3:1 | 1,1-dichloro,3-fluoropropene |
| Ex2F | trichloroethylene | methyl diflouride | 425 | 200 | 3.5:1 | 1,1-dichloro,3,3-difluoropropene |
| Ex2G | trichloroethylene | methyl triflouride | 400 | 300 | 4:1 | 1,1-dichloro,3,3,3-trifluoropropene |
| Ex2H | trichloroethylene | chlorofluoromethane | 375 | 400 | 4.5:1 | 1,1,3-trichloro,3-fluoropropene |
| Ex2I | trichloroethylene | chlorodifluoromethane | 350 | 500 | 5:1 | 1,1,3-trichloro,3,3-difluoropropene |
| Ex2J | trichloroethylene | dichlorofluoromethane | <350 | >500 | >5:1 | 1,1,3,3-tetrachloro,3-fluoropropene |
| Ex2K | 1-chloro,2,2-difluoro ethylene | methane | 550 | — | 1:1 | 1,1-difluoropropene |
| Ex2L | 1-chloro,2,2-difluoro ethylene | chloromethane | 525 | 15 | 1.5:1 | 3-chloro,1,1-difluoropropene |
| Ex2M | 1-chloro,2,2-difluoro ethylene | dichloromethane | 500 | 35 | 2:1 | 3,3-dichloro,1,1-difluoropropene |
| Ex2N | 1-chloro,2,2-difluoro ethylene | trichloromethane | 475 | 50 | 2.5:1 | 3,3,3-trichloro,1,1-difluoropropene |
| Ex2O | 1-chloro,2,2-difluoro ethylene | fluoromethane | 450 | 100 | 3:1 | 1,1,3-trifluoropropene |
| Ex2P | 1-chloro,2,2-difluoro ethylene | difluoromethane | 425 | 200 | 3.5:1 | 1,1,3,3-tetrafluoropropene |
| Ex2Q | 1-chloro,2,2-difluoro ethylene | trifluoromethane | 400 | 300 | 4:1 | 1,1,3,3,3-pentafluoropropene |
| Ex2R | 1-chloro,2,2-difluoro ethylene | chlorofluoromethane | 375 | 400 | 4.5:1 | 3-chloro,1,1,3-trifluoropropene |
| Ex2S | 1-chloro,2,2-difluoro ethylene | dichlorofluoromethane | 350 | 500 | 5:1 | 3,3-dichloro,1,1,3-trifluoropropene |
| Ex2T | 1-chloro,2,2-difluoro ethylene | chlorodifluoromethane | <350 | >500 | >5:1 | 3-chloro,1,1,3,3-tetrafluoropropene |
| Ex2U | cis1,2-dichloro,2-fluoroethylene | methane | 550 | — | 1:1 | cis-1-chloro,1,fluoro-propene |
| Ex2V | trans1,2-dichloro,2-fluoroethylene | methane | 550 | — | 1:1 | trans-1-chloro,1,fluoro-propene |
| Ex2W | cis1,2-dichloro,2-fluoroethylene | chloromethane | 525 | 20 | 1.5:1 | Cis-1,3-dichloro,1,fluoro-propene |
| Ex2X | trans1,2-dichloro,2-fluoroethylene | chloromethane | 525 | 20 | 1.5:1 | trans-1,3-dichloro,1,fluoro-propene |
| Ex2Y | cis1,2-dichloro,2-fluoroethylene | dichloromethane | 500 | 35 | 2:1 | cis-1,3,3-trichloro,1,fluoro-propene |
| Ex2Z | trans1,2-dichloro,2-fluoroethylene | dichloromethane | 500 | 35 | 2:1 | trans-1,3,3-trichloro,1,fluoro-propene |
| Ex2AA | cis1,2-dichloro,2-fluoroethylene | trichloromethane | 475 | 50 | 2.5:1 | cis-1,3,3,3-tetrachloro,1,fluoro-propene |
| Ex2BB | trans1,2-dichloro,2-fluoroethylene | trichloromethane | 475 | 50 | 2.5:1 | trans-1,3,3,3-tetrachloro,1,fluoro-propene |
| Ex2CC | cis1,2-dichloro,2-fluoroethylene | fluoromethane | 450 | 100 | 3:1 | cis-1-chloro,1,3-difluoropropene |
| Ex2DD | trans1,2-dichloro,2-fluoroethylene | fluoromethane | 450 | 100 | 3:1 | trans-1-chloro,1,3-difluoropropene |
| Ex2EE | cis1,2-dichloro,2-fluoroethylene | difluoromethane | 425 | 200 | 3.5:1 | cis-1-chloro,1,3,3-trifluoropropene |
| Ex2FF | trans1,2-dichloro,2-fluoroethylene | difluoromethane | 425 | 200 | 3.5:1 | trans-1-chloro,1,3,3-trifluoropropene |
| Ex2GG | cis1,2-dichloro,2-fluoroethylene | trifluoromethane | 400 | 300 | 4:1 | cis-1-chloro,1,3,3,3-tetrafluoropropene. |
| Ex2HH | trans1,2-dichloro,2-fluoroethylene | trifluoromethane | 400 | 300 | 4:1 | trans-1-chloro,1,3,3,3-tetrafluoropropene. |
| Ex2II | cis1,2-dichloro,2-fluoroethylene | chlorofluoromethane | 375 | 400 | 4.5:1 | cis-1,3-dichloro,1,3-difluoropropene |
| Ex2JJ | trans1,2-dichloro,2-fluoroethylene | chlorofluoromethane | 375 | 400 | 4.5:1 | trans-1,3-dichloro,1,3-difluoropropene |
| Ex2KK | cis1,2-dichloro,2-fluoroethylene | dichlorofluoromethane | 350 | 500 | 5:1 | cis-1,3,3-trichloro,1,3-difluoropropene |
| Ex2LL | trans1,2-dichloro,2-fluoroethylene | dichlorofluoromethane | 350 | 500 | 5:1 | trans-1,3,3-trichloro,1,3-difluoropropene |
| Ex2MM | cis1,2-dichloro,2-fluoroethylene | chlorodifluoromethane | <350 | >500 | >5:1 | cis-1,3-dichloro,1,3,3-trifluoropropene |
| Ex2NN | trans1,2-dichloro,2-fluoroethylene | chlorodifluoromethane | <350 | >500 | >5:1 | trans-1,3-dichloro,1,3,3-trifluoropropene |

EXAMPLE III

Certain of the Examples of Example II are repeated, while the reactor zone is exposed to pulsed or continuous laser, UV/visible, and/or microwave discharge sources, as shown in Table 3.

TABLE 3

| ID | CHCl=CX$_2$ | CH$_{4-a-b}$Cl$_a$F$_b$ | Energy source | Wave Length | Chlorinated and/or fluorinated propene |
|---|---|---|---|---|---|
| Ex2A | trichloroethylene | methyl chloride | Micro Wave | 1 m-1 mm | 1,1,3-trichloropropene |
| Ex2K | 1-chloro,2,2-difluoro ethylene | methane | Laser | 400 nm-750 nm | 1,1-difluoropropene |
| Ex2CC | cis1,2-dichloro,2-fluoroethylene | fluoromethane | UV | 100 nm-400 nm | cis-1-chloro,1,3-difluoropropene |
| Ex2FF | trans1,2-dichloro,2-fluoroethylene | Difluoro methane | Vis | 350 nm-450 nm | trans-1-chloro,1,3,3-trifluoropropene |

This invention claimed is:

1. A one-step process for the production of chlorinated and/or fluorinated propenes comprising: reacting i) a chloroethylene or a chlorofluoroethylene having the formula CHCl=CX$_2$ wherein each X is independently Cl or F; and ii) a methane, chloromethane, fluoromethane or chlorofluoromethane having the formula CH$_{4-a-b}$Cl$_a$F$_b$, wherein a is 0-3 and b is 0-3 and 4-a-b is greater than 0, to provide at least one chlorinated and/or fluorinated propene, provided that when the chloroethylene is of the formula CHCl=CCl$_2$ and the chloromethane or fluoromethane is of the formula CH$_3$Cl or CH$_3$F, the process is carried out at a temperature of less than 400° C.

2. The process of claim 1, wherein the chlorinated and/or fluorinated propene has the formula CCl$_c$F$_{2-c}$=CH—CH$_{3-e-f}$Cl$_e$F$_f$ wherein c is 0-2, e is 0-3, and f is 0-3, and 3-e-f>=0.

3. The process of claim 1, provided that when the chloroethylene or chlorofluoroethylene is of the formula CHCl=CClF or CHCl=CF$_2$ or the chloromethane or fluoromethane is not CHCl$_3$ or CH$_3$F, the process carried out at a temperature of less than 500° C.

4. The process of claim 1, wherein the process is carried out at ambient pressure or greater.

5. The process of claim 1, wherein the reaction is carried out in the presence of one or more catalyst(s) and/or initiator(s).

6. The process of claim 5, wherein the initiator comprises carbon tetrachloride, chlorine, hexachloroethane, benzotrichloride, hexachloroacetone or combinations of these.

7. The process of claim 1, wherein the methane, chloromethane, fluoromethane or chlorofluoromethane and the chloroethylene or chlorofluoroethylene are provided in a ratio of CH$_{4-a-b}$Cl$_a$F$_b$/CHCl=CX$_2$ of greater than or equal to 0.5.

8. The process of claim 4, wherein the CH$_{4-a-b}$Cl$_a$F$_b$/CHCl=CX$_2$ ratio is greater than or equal to 2.5.

9. The process of claim 1, wherein the process is conducted in an adiabatic tubular reactor.

10. The process of claim 9, wherein the reactor further makes use of a diluent to reduce the temperature within the reactor, wherein the diluent comprises an inert diluent, CH$_{4-a-b}$Cl$_a$F$_b$ or combinations of these.

11. The process of claim 1 or 3, wherein the pressure is at least 200 psig.

12. The process of claim 1, wherein the pressure is greater than 15 psig and the process is carried out in the presence of a catalyst/initiator, and the catalyst/initiator comprises chlorine or carbon tetrachloride, utilized in amounts of from 50 ppm to 100000 ppm.

13. The process of claim 11, the molar ratio of CH$_{4-a-b}$Cl$_a$F$_b$/CHCl=CX$_2$ is greater than 0.5, and the process is carried out in the presence of a catalyst or initiator.

14. The process of claim 13, wherein the pressure is at least 300 psig, the molar ratio of CH$_{4-a-b}$Cl$_a$F$_b$/CHCl=CX$_2$ is greater than 2 and the catalyst or initiator comprises chlorine or carbon tetrachloride.

15. The process of claim 14, wherein the pressure is at least 400 psig, the molar ratio of CH$_{4-a-b}$Cl$_a$F$_b$/CHCl=CX$_2$ is greater than about 2.5 and the catalyst or initiator comprises chlorine gas, hexachloroethane, benzotrichloride, hexachloroacetone, and/or carbon tetrachloromethane in an amount of from 5 ppm to 200000 ppm.

16. The process of claim 1, further comprising exposing the reaction to pulse laser, UV/visible light and/or microwave discharge.

17. A process for preparing 1,3,3,3-tetrafluoroprop-1-ene (HFO-1234ze) comprising converting a chlorinated and/or fluorinated propene prepared by the process of claim 1 into 1,3,3,3-tetrafluoroprop-1-ene (HFO-1234ze).

* * * * *

UNITED STATES PATENT AND TRADEMARK OFFICE
CERTIFICATE OF CORRECTION

PATENT NO. : 8,581,011 B2  
APPLICATION NO. : 12/900810  
DATED : November 12, 2013  
INVENTOR(S) : Max M. Tirtowidjojo et al.

Page 1 of 1

It is certified that error appears in the above-identified patent and that said Letters Patent is hereby corrected as shown below:

On the title page, item (73), Assignee, "Dow Global Technologies, LLC" should read "Dow Global Technologies LLC"

Signed and Sealed this
Fourteenth Day of October, 2014

Michelle K. Lee
*Deputy Director of the United States Patent and Trademark Office*